United States Patent [19]
de Jong

[11] Patent Number: 5,284,479
[45] Date of Patent: Feb. 8, 1994

[54] IMPLANTER

[75] Inventor: Hendrik J. de Jong, Groenlo, Netherlands

[73] Assignee: N.V. Nederlandsche Apparatenfabriek Nedap, De Groenlo, Netherlands

[21] Appl. No.: 911,389

[22] Filed: Jul. 13, 1992

Related U.S. Application Data

[63] Continuation of Ser. No. 573,566, Aug. 28, 1990, abandoned.

[30] Foreign Application Priority Data

Aug. 30, 1989 [NL] Netherlands .................. 8902186

[51] Int. Cl.$^5$ ............................................. A61M 31/00
[52] U.S. Cl. ................................. 604/60; 604/130; 604/137; 604/63; 606/117
[58] Field of Search .................. 604/98–100, 604/110, 95, 130, 134, 135, 137, 189, 60–64, 59, 48; 606/116, 117; 206/532, 534.1, 628, 537

[56] References Cited

U.S. PATENT DOCUMENTS

| | | | |
|---|---|---|---|
| 842,631 | 1/1907 | Deperdussin | 604/64 |
| 3,430,626 | 3/1969 | Bergman | 128/218 |
| 3,494,358 | 2/1970 | La Verne Fehlis | 604/137 |
| 3,744,493 | 7/1973 | Booher et al. | 128/217 |
| 4,031,889 | 6/1977 | Pike | 604/144 |
| 4,105,030 | 8/1978 | Kereso | 604/61 |
| 4,263,910 | 4/1981 | Pardekooper | 604/60 |
| 4,474,308 | 10/1984 | Bergeron | 604/59 |
| 4,820,267 | 4/1989 | Harman | 604/60 |
| 4,941,874 | 7/1990 | Sandow | 604/60 |
| 4,990,136 | 2/1991 | Geria | 604/63 |
| 4,994,028 | 2/1991 | Leonard | 604/59 |

Primary Examiner—Robert A. Hafer
Assistant Examiner—David J. Kenealy
Attorney, Agent, or Firm—Jacobson, Price, Holman & Stern

[57] ABSTRACT

An implanter for implanting an implant (3) in an animate being (14) includes a housing (15) on which the inner end of a hollow injection needle (2) is mounted, a plunger (6) mounted in the housing and adapted to extend into the hollow needle through the inner end of the needle, and a locking element (8, 32) for engaging with and retaining the plunger (6) against the force of compression spring (7) in a position where the plunger extends into the hollow needle for a predetermined distance. The locking element is part of a release device (9, 10; 30, 31, 33) which abuts the body (14) of the animate being when the injection needle has been introduced into the body to a predetermined depth to automatically unlock the locking element. The plunger is then forced by the spring (7) against an implant (3) disposed in operation in the injection needle for retaining the implant in the body when the injection needle is retracted from the body.

19 Claims, 3 Drawing Sheets

IMPLANTER

This is a continuation of application Ser. No. 07/573,566, filed Aug. 28, 1990, which was abandoned upon the filing hereof.

BACKGROUND OF THE INVENTION

The invention relates to an implanter for implanting an implant in an animate being, the implanter a housing mounting one end of a hollow injection needle is mounted and a plunger in the housing adapted to extend into the hollow needle from the one end of the hollow injection needle that is mounted in the housing.

Such an implanter is known from U.S. Pat. No. 3,744,493 and can be used for implanting via the hollow injection needle a usually cylindrical implant, containing for instance a medicinal preparation or an electronic circuit for remote detection, in animate beings, such as cattle.

A drawback of the known implanter is that two different operations are required for introducing the injection needle and subsequently introducing the implant into the body of an animate being via the injection needle. First the injection needle is stuck into the body and then the implant is introduced into the body via the injection needle by means of a plunger. On the one hand, this takes relatively much time, which may pose a problem, an animal during treatment being somewhat excited as it is and hence being capable of jerky movements. Moreover there is a real chance that the person who carries out the implantation, for the very reason of carrying out the operation as swiftly as possible, retracts the needle too soon, i.e. before the needle has been introduced deep enough, or that the animal recoils somewhat precisely during the operation. The depth at which the implant is lodged in the body may then be undesirably small, there being a chance the animal will lose the implant. This is particularly important when the implant contains an identification chip which is to remain in the body for a long time.

Further, U.S. Pat. No. 4,820,267 discloses an implanter which comprises a plunger fixedly mounted in the housing and a hollow injection needle movable relatively to the plunger. After having been introduced into the body of for instance an animal, the injection needle is manually retracted into the housing with the fixed plunger retaining an implant disposed in the injection needle, so that it remains behind in the body. This known device, too, involves the risk of the needle being retracted too soon, as a result of which the implant is not properly introduced.

It is observed that U.S. Pat. No. 3,430,626 discloses a device for injecting fluids into cattle by means of an injection needle, the device comprising bar-shaped driving means which in operation force the fluid to be injected into the injection needle but which are normally arrested in an inoperative position. The device further comprises a feeler mounted with a spring and extending beyond the tip of the injection needle, which upon introduction of the injection needle into the body of an animal moves in a rearward direction relatively to the injection needle and thus unlocks the driving means. Under the influence of the force exerted by a coil spring the driving means then force the fluid to be injected into the injection needle.

In this known device the driving means are unlocked when the injection needle has only barely, if at all, penetrated the animal's skin. Moreover, the driving means are designed to actually force the fluid to be injected through the injection needle introduced into the body, which takes some time. Accordingly, in this known device, too, there is a real chance that the injection needle is retracted too soon and the injection operation will not have the desired result.

BRIEF SUMMARY OF THE INVENTION

The object of the invention is to overcome the drawbacks outlined hereinabove and generally to provide an implanter that is easy to operate but functions reliably.

To this effect an implanter of the type described hereinabove is characterized according to the invention by locking means for retaining the plunger against the pressure of spring means in a position where the plunger extends into the hollow needle over a predetermined distance, the locking means comprising release means which abut the body of the animate being when the injection needle has been introduced into the body to a predetermined depth and subsequently automatically releases the locking means, causing the plunger to be pressed by the spring means against an implant disposed in operation in the injection needle for retaining the implant in the body when the injection needle is being retracted therefrom;

BRIEF DESCRIPTION OF THE DRAWINGS

The invention will now be further described in detail with reference to the accompanying drawings of some embodiments, wherein.

DETAILED DESCRIPTION

Figure 1:
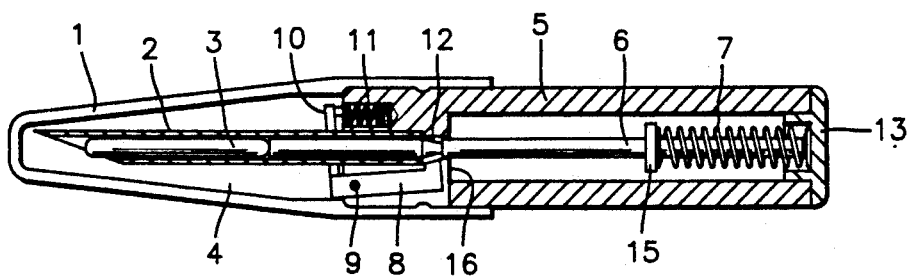
FIG. 1 is a schematic longitudinal cross sectional view of an embodiment of an implanter according to the invention.

FIG. 1 schematically shows a longitudinal cross sectional view of a first embodiment of an implanter according to the invention. The implanter shown comprises a hollow needle 2, which is preferably protected by a detachable cap 1 when the implanter is not being used.

An implant 3 has already been provided in the needle 2. In the space 4 a disinfectant fluid or paste may be provided to prevent wound infections after the implantation.

The needle 2 can be mounted on a housing 5 and is optionally mounted for rapid detachment, for instance by means of a bayonet catch. In the embodiment shown the housing has a substantially cylindrical form and is hollow. Provided in the housing is a plunger 6 which extends into the hollow needle over a predetermined distance and can be moved to the left, i.e. into the needle, by means of a pressure spring 7 pressing against a shoulder 15 of the plunger, but which plunger is retained by locking arm member 8 adapted to pivot about a pin 9. Disposed at the end of the housing which faces towards the outer part a needle 2 is a pressure plate 10 which, in this embodiment, forms one whole integral element with lock 8 and (as shown) is pressed to the left by a spring 11, thus pressing lock 8 into a groove 12 of the plunger 6. Further, the housing 5 is closed by a cover 13 supporting the spring 7.

Figure 2:
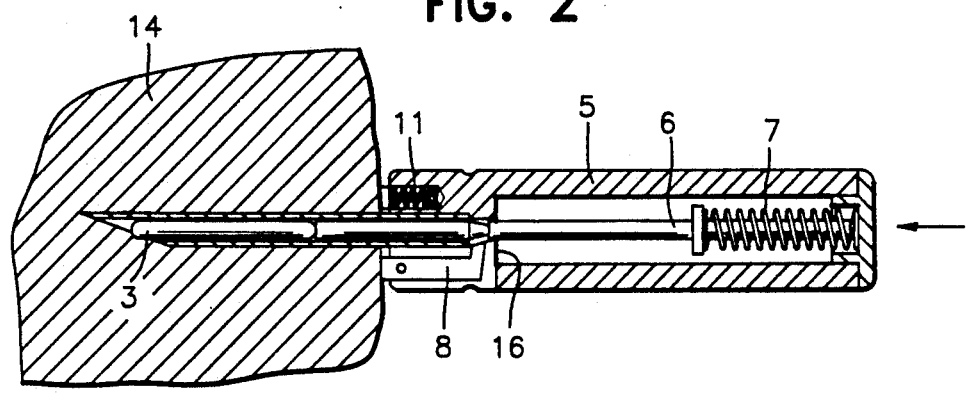
FIGS. 2-4 are cross-sectional views which schematically show in what way an implant can be introduced into a body using an implanter according to the invention.

FIG. 2 shows the situation where the needle 2 has been introduced into the body 14 to the proper depth. The lock 8 now releases the plunger 6 due to the pressure plate 10 pressing against body 14, the spring 11 thus being compressed and the lock pivoting clockwise about the pin 9.

Figure 3:
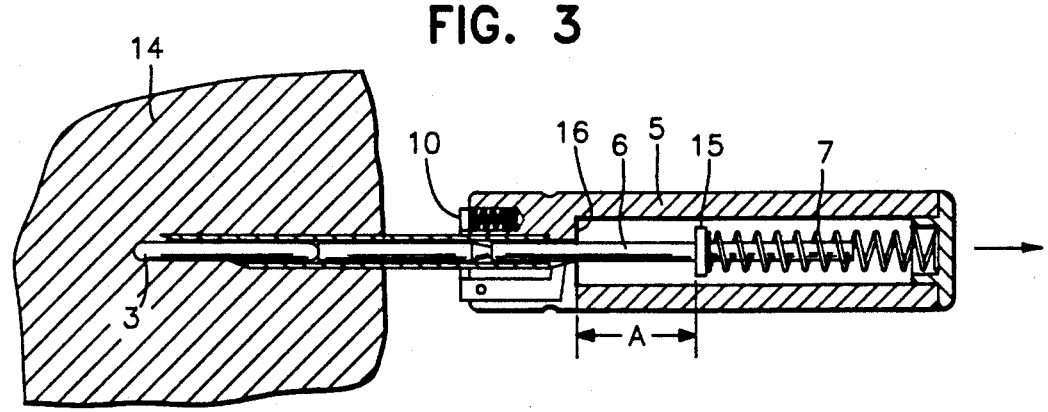
Figure 4:
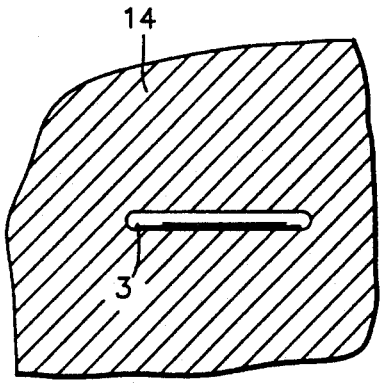

During the subsequent retractive motion the plunger 6 continues to retain the implant 3 in its position within the body owing to the expansion of spring 7 (FIG. 3). Distance A between the shoulder 15 and the inner end wall 16 of the housing proximal to the needle diminishes and will = 0 at the moment when the implant is no longer surrounded by the needle 2 and thus will of itself remain behind in the body (FIG. 4). Thus the implanting operation has been completed swiftly and without fault. The implanter can now be disposed of or be prepared for reuse. An important advantage of an implanter according to the invention is that the plunger 6 is automatically actuated as soon as the needle has been introduced into the body to sufficient depth. Moreover, the plunger only has to retain the implant during the retraction of the needle, but need not actively force the implant from the needle. Implantation of the implant at insufficient depth is prevented and also during the implantation no further operations are necessary in addition to introducing and retracting the needle.

The implanter can be prepared for reuse by bringing plunger 6 into the initial position by means of a bar-shaped auxiliary device, after which a new implant 3 can be provided in needle 2. Clearly, this must be effected aseptically and new disinfectant fluid or paste must be provided. To facilitate the above operation and to ensure asepsis, according to the invention a special holder can be used which may contain a plurality of implants and disinfectants.

Figure 5:
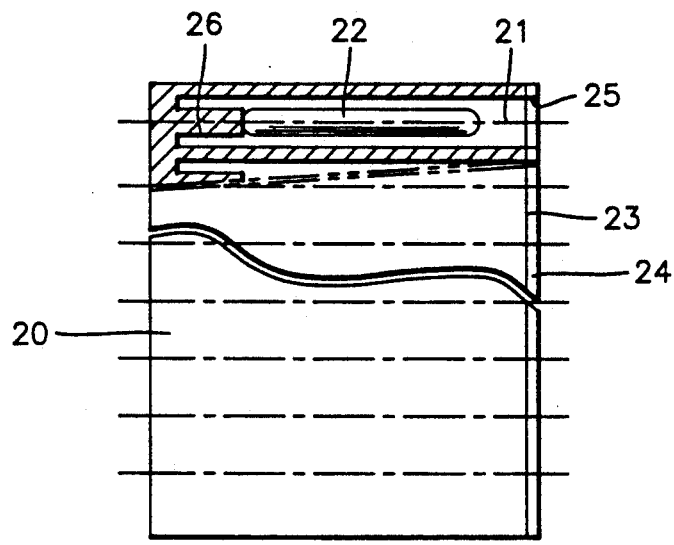
FIG. 5 is a part cross-sectional view which shows a holder for implants, to be used with an implanter according to the invention.

FIG. 5 schematically shows an embodiment of such a holder 20. One of the holes 21 for receiving an implant is shown in section with an implant 22 disposed therein. The hole 21 may be partly filled with a disinfectant fluid or paste. At one end the hole is closed by means of a foil 23. Provided at the other end and extending into the hole 21 is a pressure finger 26. The purpose of the pressure finger will be further explained hereinbelow.

Figure 6:
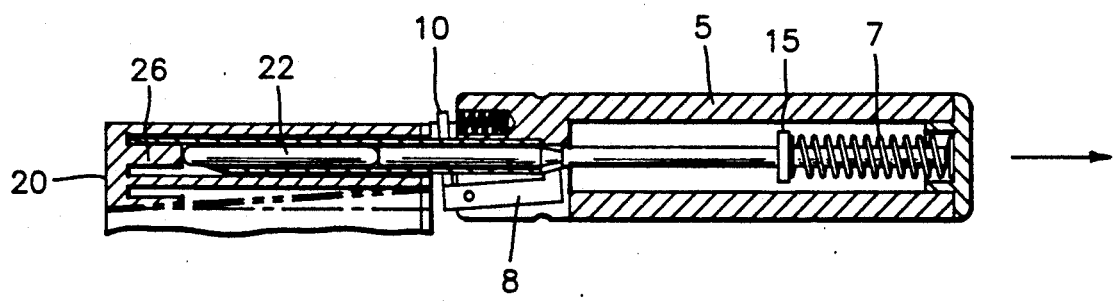
FIG. 6 schematically illustrates in cross section the loading of an implanter of FIGS. 1-4 according to the invention using a holder according to FIG. 5.

FIG. 6 illustrates in what way the reloading of the implanter is accomplished. To that end the needle 2 of the implanter penetrates through the foil 23 into the hole 21. Upon further displacement of needle 2 into hole 21 the implant 22 is taken up into needle 2, the optional disinfectant moistening the needle internally and externally. In the process, pressure finger 26 pushes the plunger 6 into the housing 5 via the implant, thus compressing spring 7. When the needle has almost reached the bottom of hole 21, the lock 8 engages groove 12 again. Upon retraction of the needle from hole 21 the implant is carried with it and the implanter is ready for use again. If so desired, for each use the needle can be replaced by a new one.

The exact location of the desired hole 21 by injection needle 2 can be facilitated by mounting a centering plate 24 provided with—optionally slightly conical—bores 25 guiding the injection needle in penetrating a hole 21. In a particular embodiment the foil 23 and the centering plate 24 may be formed as one whole; the foil portions 23 are then, for instance, formed as the thinner parts of a plastic centering plate 24.

Figure 7:
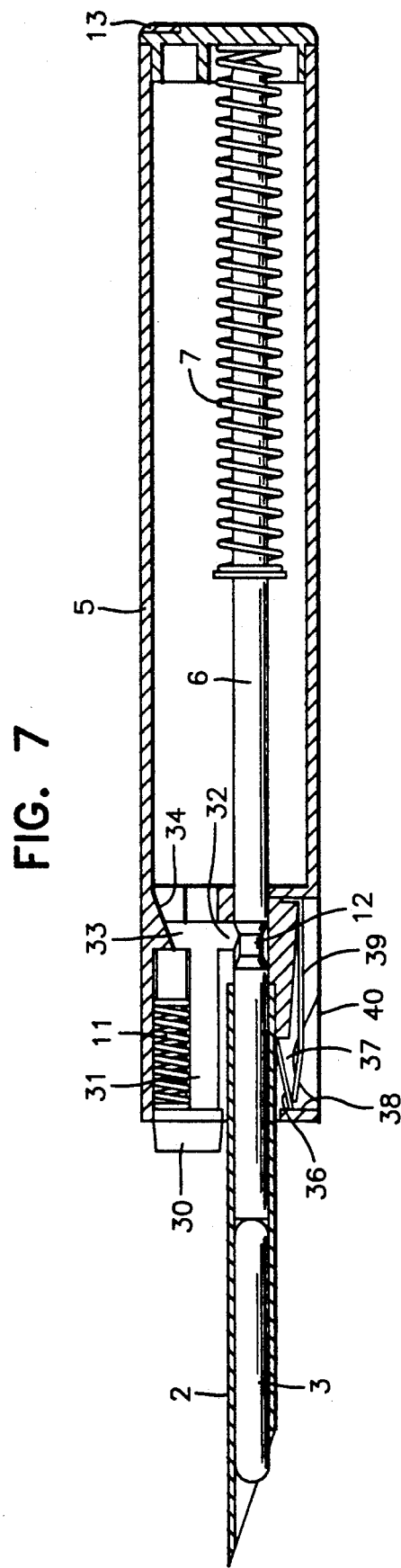
FIG. 7 is a schematic longitudinal cross sectional view of another embodiment of an implanter according to the invention.

Further, FIG. 7, by way of example, shows a longitudinal sectional view of a second embodiment of an implanter according to the invention. Corresponding parts are given the same reference numerals as in FIGS. 1-3. In the embodiment of FIG. 7, instead of the pivoting pressure plate 10 of FIG. 1, a pressure button 30 is used which is pressed outwardly by means of a pressure spring 11 mounted in the housing 5. Extending rearwardly from the rear side of the pressure button is the free end of a bar or strip shaped locking member 31 comprising at the end away from the pressure button a first projection 32 engaging when inoperative the groove 12 of the plunger 6. Although the projection 32 and the groove 12 both have bevelled edges in this embodiment, the projection is nevertheless prevented from slipping from the groove under the influence of the force exerted by the spring 7, because opposite to the projection 32 a second projection 33 is provided which rests against a projection surface 34 of the housing, this surface 34 extending obliquely inwardly towards the front of the housing.

However, the locking member 31 can move further into the housing when the pressure button 30 abuts the body of an animal and the spring 11 is compressed. Due to the fact that the projection surface 34 extends in the rearward direction precisely obliquely outwardly, the projection 33 is permitted to move slightly off the plunger 6 upon a rearward movement of the locking member 31, as a result of which the projection 32 leaves the groove 12. The plunger is then released again and will retain the implant in the manner described before while the needle is being retracted.

In the embodiment shown the needle is detachably mounted in the housing. To that end the needle comprises at least one spring element 36 operating as a barb, adapted to spring away from the needle in a chamber 37 formed in the housing, so that its front end will abut the front wall 38 of the chamber.

Further, mounted in the chamber is a needle unlocking member 39, plate-shaped in this embodiment, adapted to be pressed against the spring element 36 with the thumb. To that end a recess 40 in housing 5 for operating the needle unlocking member is provided. When in this manner the spring element is pressed against the needle, the needle can be pulled from the housing.

It is observed that after perusal of the above, various modifications will readily occur to a person skilled in the art. Thus, the locking member 32 may form one integral element with the pressure button 30, or, conversely, be a separate element. Further, instead of the compression springs 7 and/or 11, other types of springs can be used, such a leaf springs or extension springs.

Also, it is not necessary for the housing 5 to be closed throughout its circumference These and similar modifications are considered to fall within the scope of the invention.

What I claim is:

1. An implanter for implanting an implant in an animate being, comprising:
   a housing having a forward end and a rearward end;
   a hollow injection needle projecting from said forward end of said housing and having an inner end portion mounted in said forward end of said housing and a tip end remote from said housing, said needle being adapted to contain an implant in sliding relationship therein and to facilitate ejecting the implant from said needle;

a plunger movably mounted in said housing and having a forward end portion engageable through said inner end of said hollow needle for abutting relationship against an implant in said needle;

plunger spring means in said housing for resiliently urging at least the forward end of said plunger through at least part of said hollow needle; and releasable locking means comprising a locking groove in said plunger, a locking arm engageable with said locking groove for retaining said plunger against the force of said plunger spring means in a position where said forward end of said plunger extends in said inner end portion of said hollow needle for a predetermined distance, a pressure member pivotally mounted at said forward end of said housing by a pivot pin extending in said housing transversely to the longitudinal direction of said hollow needle and connected to said locking arm, and a locking spring between said forward end of said housing and said pressure member for urging said locking arm into engagement in said groove of said plunger, so that when said hollow needle is inserted into a body of an animate being to a predetermined depth said pressure member abuts said body of said animate being and is pressed against the force of said locking spring to pivot said pressure member and said locking arm about said pivot pin and disengage said locking arm from said locking groove in said plunger whereby said plunger spring means urges said plunger against said implant for retaining said implant in said body at said predetermined depth when said injection needle is retracted from said body.

2. The implanter as claimed in claim 1 and further comprising:
a plunger spring support member on said rearward end of said housing;
shoulder means on said plunger between said locking groove and said support member; and
said plunger spring being mounted between said plunger spring support member and said shoulder means.

3. The implanter as claimed in claim 2 wherein:
said housing has a hollow interior portion;
said plunger, shoulder means and plunger spring means are within said hollow interior portion of said housing; and
said plunger spring support member comprises a closing member for closing said hollow interior portion of said housing at said rearward end thereof.

4. The implanter as claimed in claim 1 and further comprising:
a cap member releasably attachable to said housing for enclosing and protecting said hollow injection needle when not in use; and
a disinfectant in said cap when mounted on said housing.

5. The implanter as claimed in claim 2 and further comprising:
a cap member releasably attachable to said housing for enclosing and protecting said hollow injection needle when not in use; and
a disinfectant in said cap when mounted on said housing.

6. The implanter as claimed in claim 3 and further comprising:
a cap member releasably attachable to said housing for enclosing and protecting said hollow injection needle when not in use; and
a disinfectant in said cap when mounted on said housing.

7. The implanter as claimed in claim 1 wherein:
a locking spring chamber is provided in said housing; and
said locking spring is mounted in said spring chamber and resiliently urges said pressure member a predetermined distance outwardly from said forward end of said housing in the direction of said tip end of said injection needle.

8. An implanter for implanting an implant in an animate being, comprising:
a housing having a forward end and a rearward end;
a hollow injection needle projecting from said forward end of said housing and having an inner end portion mounted in said forward end of said housing and a tip end remote from said housing, said needle being adapted to contain an implant in sliding relationship therein to facilitate ejecting the implant from said needle;
a plunger movably mounted in said housing and having a forward end engageable through said inner end portion of said hollow needle for abutting relationship against an implant in said needle;
plunger spring means in said housing for resiliently urging at least the forward end of said plunger through at least part of said hollow needle; and
releasable locking means comprising a locking arm engageable with said plunger for releasably retaining said plunger against the force of said plunger spring means in a position where said plunger extends in said inner end of said hollow needle for a predetermined distance, and release means on said forward end of said housing cooperating with said locking arm and engageable in abutting relationship with said body of said animate being when said injection needle has been injected into said body to a predetermined depth for automatically releasing said locking arm so that said plunger is urged by said plunger spring means against an implant in said injection needle for retaining said implant in said body at said predetermined depth when said injection needle is retracted from said body;
a forward chamber in said forward end of said housing;
a front wall on said forward end of said housing having an opening therein for receiving said needle;
at least one spring barb on said inner end of said injection needle extending radially outwardly from said injection needle into said forward chamber when said injection needle is mounted in said housing for releasably engaging said front wall on said forward end of said housing to prevent removal of said needle through said opening in said front wall; and
a needle releasing member mounted on said forward end of said housing and engageable with said at least one spring barb so that pushing said needle release member against said at least one spring barb pushes said at least one spring barb against said injection needle to disengage said at least one spring barb from said front wall whereby said needle and at least one spring barb are removable from said forward end of said housing through said opening in said front wall.

9. The implanter as claimed in claim 8 wherein said releasable locking means further comprises:
a locking groove in said plunger;
said locking arm comprising an elongate locking arm in said forward end of said housing and movable in a direction parallel to said longitudinal direction of said injection needle;
said release means comprising a pressure member movable parallel to the longitudinal direction of said hollow injection needle and connected to said locking arm;
a first projection on said elongate locking arm engageable with said groove in said plunger in a locking position;
a projection surface on said housing extending obliquely inwardly in the direction of said forward end of said housing; and
a second projection on said elongate locking arm projecting in a direction opposite to said first projection and cooperatively slidably engageable with said projection surface for urging said first projection into locking engagement with said groove in said locking position, so that when said pressure member engages in abutting relationship said body of said animate being at said predetermined depth of said needle, said pressure member is pushed by said body in the direction of said housing and pushes said elongate locking arm towards said rearward end of said housing whereby said second projection slides along said projection surface allowing said first projection to move radially outwardly relative to said plunger to disengage from said groove so that said plunger spring means pushes said plunger through at least part of said injection needle for ejecting an implant from said needle into said body at said predetermined depth when said injection needle is retracted from said body.

10. The implanter as claimed in claim 9 and further comprising:
pressure member spring means in said forward end of said housing for resiliently urging said pressure member a predetermined distance outwardly from said forward end of said housing in the direction of said tip end of said injection needle.

11. An implanter for implanting an implant in an animate being, comprising:
a housing having a forward end and a rearward end;
a hollow injection needle projecting from said forward end of said housing and having an inner end portion mounted in said forward end of said housing and a tip end remote from said housing, said needle being adapted to contain an implant in sliding relationship therein and to facilitate ejecting the implant from said needle;
a plunger movably mounted in said housing and having a forward end engageable through said inner end portion of said hollow needle for abutting relationship against an implant in said needle;
plunger spring means in said housing for resiliently urging at least the forward end of said plunger through at least part of said hollow needle; and
releasable locking means comprising a locking groove in said plunger, an elongate locking arm movable in said housing, a first projection on said locking arm engageable with said locking groove for releasably retaining said plunger against the force of said plunger spring means in a locking position where said plunger extends in said inner end of said hollow needle for a predetermined distance, a second projection on said elongate locking arm projecting in a direction opposite to said first projection, a projection surface in said housing extending obliquely inwardly in the direction of said forward end of said housing and engageable with said second projection for urging said first projection into engagement with said locking groove when said plunger is in said locking position, and release means on said forward end of said housing comprising a pressure member movable parallel to the longitudinal direction of said needle and connected with said elongate locking arm, said pressure member being engageable in abutting relationship with a body of said animate being when said injection needle has been injected in said body to a predetermined depth for automatically releasing said second projection from a locking position with said projection surface and said first projection from said locking groove so that said plunger is urged by said plunger spring means against an implant in said injection needle for retaining said implant in said body at said predetermined depth when said injection needle is retracted from said body.

12. The implanter as claimed in claim 11 and further comprising:
pressure member spring means in said forward end of said housing for resiliently urging said pressure member a predetermined distance outwardly from said forward end of said housing in the direction of said tip end of said injection needle.

13. The implanter as claimed in claim 11 and further comprising:
a plunger spring support member on said rearward end of said housing;
shoulder means on said plunger between said locking groove and said support member; and
said plunger spring being mounted between said plunger spring support member and said shoulder means.

14. The implanter as claimed in claim 13 wherein:
said housing has a hollow interior portion;
said plunger, shoulder means and plunger spring means are within said hollow interior portion of said housing; and
said plunger spring support member comprises a closing member for closing said hollow interior portion of said housing at said rearward end thereof.

15. The implanter as claimed in claim 11 and further comprising:
a cap member releasably attachable to said housing for enclosing and protecting said hollow injection needle when not in use; and
a disinfectant in said cap when mounted on said housing.

16. The implanter as claimed in claim 13 and further comprising:
a cap member releasably attachable to said housing for enclosing and protecting said hollow injection needle when not in use; and
a disinfectant in said cap when mounted on said housing.

17. The implanter as claimed in claim 14 and further comprising:
 a cap member releasably attachable to said housing for enclosing and protecting said hollow injection needle when not in use; and
 a disinfectant in said cap when mounted on said housing.

18. The implanter as claimed in claim 11 and further comprising:
 pressure member spring means in said forward end of said housing for resiliently urging said pressure member a predetermined distance outwardly from said forward end of said housing in the direction of said tip end of said injection needle.

19. The implanter as claimed in claim 13 and further comprising:
 pressure member spring means in said forward end of said housing for resiliently urging said pressure member a predetermined distance outwardly from said forward end of said housing in the direction of said tip end of said injection needle.

* * * * *